U nited States Patent [19]
Vorbrügen et al.

[11] Patent Number: 4,468,395
[45] Date of Patent: Aug. 28, 1984

[54] PROSTAGLANDINS AND PROSTACYCLINS, PROCESSER FOR THEIR PREPARATION AND THEIR USE AS MEDICAMENTS

[75] Inventors: Helmut Vorbrügen; Walter Elger; Michael-Harold Town; Ekkehard Schillinger, all of Berlin, Fed. Rep. of Germany

[73] Assignee: Schering, Aktiengesellschaft, Berlin and Bergkamen, Fed. Rep. of Germany

[21] Appl. No.: 380,326

[22] Filed: May 20, 1982

Related U.S. Application Data

[63] Continuation-in-part of Ser. No. 367,869, Apr. 13, 1982, abandoned.

[30] Foreign Application Priority Data

Apr. 13, 1981 [DE] Fed. Rep. of Germany ....... 3115997
Nov. 13, 1981 [DE] Fed. Rep. of Germany ....... 3145830

[51] Int. Cl.³ .................. C07D 263/14; C07D 233/14; C07D 277/10; A61K 31/42
[52] U.S. Cl. ............................ 424/246; 260/239 BC; 260/330; 260/330.6; 424/248.57; 424/251; 424/273 R; 424/272; 424/270; 424/269; 544/53; 544/55; 544/88; 544/96; 544/97; 544/331; 544/332; 544/335; 544/333; 548/146; 548/181; 548/186; 548/224; 548/336; 548/337; 548/342; 548/237
[58] Field of Search ............... 562/121, 119; 502/503, 502/501; 544/53, 55, 88, 96, 97, 331, 332, 333, 335; 542/426, 430, 431; 548/146, 181, 186, 229, 237, 336, 337, 342; 260/239 BC, 330, 330.6; 424/269, 272, 270, 233 R, 251, 248.57, 246

[56] References Cited

FOREIGN PATENT DOCUMENTS 2013661 8/1979 United Kingdom ................ 560/119

OTHER PUBLICATIONS

European Search Report No. 0034778 for EP 81 10 1037, dated 11-05-1981.
Angew. Chem. Int. Ed. Engl. 19, Oct. 1980, pp. 749, 819, 820.

Primary Examiner—Robert Gerstl
Attorney, Agent, or Firm—Millen & White

[57] ABSTRACT

Compounds of Formula I

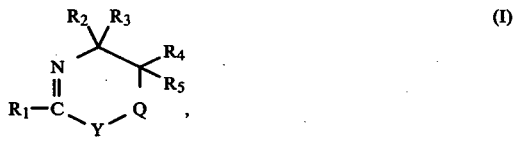

wherein
$R_1$ is a prostaglandin or prostacyclin residue;
Y is oxygen, sulfur, imino, or N-($C_1$-$C_4$-alkyl) imino;
Q is $(CR_6R_7)_p$ wherein p is an integer of 0 to 3;
$R_2$ is hydrogen; alkyl of 1–6 carbon atoms optionally substituted by hydroxy or amino; $C_1$-$C_4$-alkoxycarbonyl; benzyloxycarbonyl; cyano; or di-$C_1$-$C_4$-alkylaminocarbonyl;
$R_3$, $R_4$, $R_5$, $R_6$ and $R_7$ each independently is hydrogen; alkyl of 1–6 carbon atoms optionally substituted by hydroxy or amino; or aryl; and
$R_3$ and $R_4$ together form a trimethylene, tetramethylene, or 1,3-butadienylene group when $R_2$ and $R_5$ together represent a direct bond;

have valuable pharmacological properties, e.g., as blood-pressure-lowering or abortive agents.

25 Claims, No Drawings

PROSTAGLANDINS AND PROSTACYCLINS, PROCESSER FOR THEIR PREPARATION AND THEIR USE AS MEDICAMENTS

CROSS REFERENCE TO RELATED APPLICATION

This application is a continuation-in-part of U.S. application Ser. No. 367,869 filed on Apr. 13, 1982, now abandoned whose disclosure is incorporated by reference herein.

BACKGROUND OF THE INVENTION

The present invention relates to novel prostaglandins and prostacyclins, a process for their preparation and their use as medicinal agents.

As biological conversion products of triply-, quadruply- (arachidonic acid), and quintuply-unsaturated, naturally occurring $C_{20}$-fatty acids, great therapeutic significance is attributed, above all, to prostaglandins, prostacyclins, and thromboxanes, especially in the form of their analogs.

The functionality of their 1-carboxy group is of great importance for the interaction of these compounds with receptors, i.e., with respect to selectivity and duration of biological efficacy, as well as for metabolism ($\beta$-oxidation). Compared with the 1-carboxylic acids, the 1-esters, 1-amides, and, especially, 1-sulfonamides or 1-acylamides show a different spectrum of biological activity [see, inter alia, T. K. Schaaf and H. J. Hess, J. Med. Chem. 22: 1340 (1979)].

However, all of these groups are either neutral, such as the 1-esters or 1-amides, or they are acidic, such as the 1-acylsulfonamides. Thus, there has been great interest in converting the 1-carboxy group in prostaglandins, prostacyclins, and thromboxanes, as well as the analogs thereof, into alkaline derivatives without changing their valence.

It is now readily possible, with the aid of a new method described in PCT/DE81/00225, filed Dec. 14, 1981, whose disclosures are incorporated by reference herein, to convert the 1-carboxy group of prostaglandins and prostacyclins, as well as the derivatives thereof, into the corresponding basic $\Delta^2$-oxazolines, $\Delta^2$-thiazolines and $\Delta^2$-imidazolines, respectively, as well as into their higher-membered analogs, such as, for example, 5,6-dihydro-4H-1,3-oxazines, 5,6-dihydro-4H-1,3-thiazines, and tetrahydropyrimidines.

These novel derivatives have a different and more selective spectrum of biological efficacy and, especially in the case of the prostacyclins, are chemically and metabolically considerably more stable and thus of longer duration of efficacy than prostacyclin ($PGI_2$).

SUMMARY OF THE INVENTION

It is, accordingly, an object of this invention to provide new such compounds having advantageous properties of the same nature.

Upon further study of the specification and appended claims, further objects and advantages of this invention will become apparent to those skilled in the art.

These objects have been attained by providing prostaglandins of Formula I

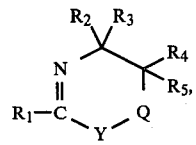

wherein $R_1$ is a prostaglandin residue of the formula

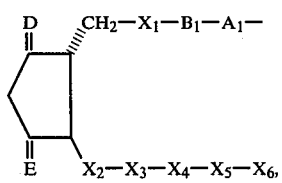

wherein for $-X_1-B_1-A_1-$, the following combinations are possible, (a) $A_1$ is $-(CH_2)_n-$, $-(CH_2)_m-O-$, or $-CF_2-(CH_2)_m-$, wherein n is an integer of 1-3 and m is an integer of 1-2, or is $-CH=CH-CH_2-$ or $-CH_2-CH=CH$, and $X_1-B_1$ is $-(CH_2)_3-$ or $-CH=C=CH-$;

(b) $X_1-B_1-A_1$ is $-(CH_2)_5-$;

(c) $B_1-A_1$ is $-(CH_2)_o-$, $-(CH_2)_n-O-$, $-CF_2-(CH_2)_n-$, $-CH=CH-(CH_2)_m-$, or $-(CH_2)_m-CH=CH$, wherein m is 1-2, n is 1-3, and o is 1-4, and $X_1$ is cis-alkenylene of the formula

wherein $R_8$ and $R_9$ each independently is hydrogen or $C_1-C_6$-alkyl; and (d) $A_1$ is $-CH_2-$, $B_1$ is oxygen or $-CH_2-$, and $X_1$ is m-phenylene;

D is oxygen; hydrogen and $\alpha$- or $\beta$-hydroxy; hydrogen and $\alpha$- and $\beta$-halogen; or $CH_2$;

E is oxygen; hydrogen and $\alpha$-hydroxy; hydrogen and $\alpha-CH_3$; or hydrogen and $\alpha-CH_2OH$;

$X_2$ is $-CH_2-CH_2-$, $-C\equiv C-$, or trans-alkenylene of the formula

wherein $R_8$ and $R_9$ are as defined above, $X_3$ is

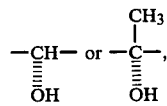

$X_4$ is $-(CH_2)_n-$ wherein n is 1-3, or

wherein $R_{10}$ and $R_{11}$ each independently is hydrogen, fluorine, methyl or methoxy, or $R_{10}$ and $R_{11}$ jointly represent —$CH_2$—$CH_2$— or —$CH_2$—$CH_2$—$CH_2$—, $X_5$ is —$CH_2$—, oxygen, sulfur, or a direct bond; and $X_6$ is phenyl, 3- or 4-chlorophenyl, 3-trifluoromethylphenyl, α- or β-naphthyl, 2- or 3-furyl, 2- or 3-thienyl, 2-, 3-, or 4-pyridyl or, when $X_5$ is a direct bond, $X_6$ is

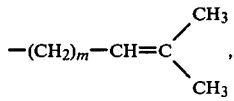

—$(CH_2)_m$—C≡C—$CH_3$ or —$(CH_2)_m$—C≡C—$CH_2$—$CH_3$, wherein m is 1 or 2, —$(CH_2)_4$—$OCH_3$, —$CH(CH_3)$—$CH_2$—$CH_2$—$CH_3$ or —$(CH_2)_3$—CH=$CH_2$; or $R_1$ is a prostacyclin residue of the formula

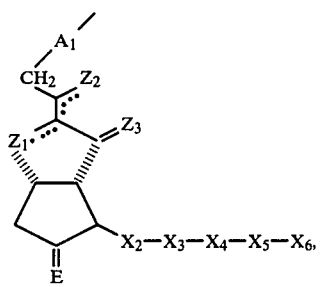

wherein

E and $X_2$–$X_6$ are as defined above and $A_1$ is as defined above in (a);

$Z_3$ is $H_2$ or oxygen; and (i) $Z_1$ is oxygen or $CH_2$ when $Z_2$ is hydrogen or cyano, and (ii) $Z_1$ is nitrogen when $Z_2$ is $H_2$; or $R_1$ is a prostacyclin residue of the formula

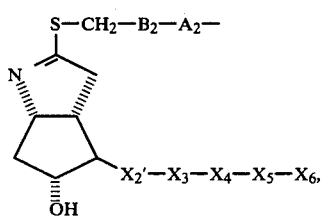

wherein $A_2$ is —$CH_2$—, —$CF_2$—, or

or when $B_2$ is a direct bond, $A_2$ also can be trans-alkenylene of the formula

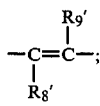

$B_2$ is —$CH_2$— or a direct bond;

$X_2'$ is —$CH_2$—$CH_2$—, —C≡C—, or trans-alkenylene of the formula

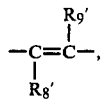

wherein each of $R_8'$ and $R_9'$ in each foregoing instance is independently hydrogen or fluorine, and $X_3$–$X_6$ are as defined above, and Y is oxygen, sulfur, imino, or N—($C_1$–$C_4$-alkyl) imino, Q is $(CR_6R_7)_p$ wherein p is an integer of 0 to 3, $R_2$ is hydrogen; alkyl of 1-6 carbon atoms optionally substituted by hydroxy or amino; $C_1$–$C_4$-alkoxycarbonyl; benzyloxycarbonyl; cyano; or di-$C_1$–$C_4$-alkylaminocarbonyl;

$R_3$, $R_4$, $R_5$, $R_6$ and $R_7$ each independently is hydrogen; alkyl of 1-6 carbon atoms optionally substituted by hydroxy or amino, or aryl; and $R_3$ and $R_4$ together can also form trimethylene, tetramethylene, or 1,3-butadienylene when $R_2$ and $R_5$ jointly represent an additional bond.

DETAILED DISCUSSION

Suitable $R_2$, $R_3$, $R_4$, $R_5$, $R_6$, $R_7$, $R_8$, $R_9$, and $R_{12}$ (see below) alkyl moieties of 1-6 carbon atoms, include methyl, ethyl, propyl, isopropyl, butyl, isobutyl, sec-butyl, tert-butyl, pentyl, isopentyl, hexyl, isohexyl, etc., all of which can optionally be substituted by hydroxy, amino, nitro, fluorine, chlorine, bromine, $C_1$–$C_4$-alkoxycarbonyl, di-$C_1$–$C_4$-alkylaminocarbonyl, $C_1$–$C_4$-alkylaminocarbonyl, tri-$C_1$–$C_4$-alkylsilyloxy, tetrahydropyranyloxy, or benzoyloxy, preferably by hydroxy, amino, or chlorine. Preferred alkyl residues for $R_2$–$R_9$ and $R_{12}$ are those of 1-4 carbon atoms. These alkyl residues can likewise be substituted, preferably by hydroxy or amino.

For the Y N-alkyl embodiment, suitable alkyl residues include those of 1-4 carbon atoms which are disclosed above, for example, in connection with $R_2$.

Suitable aryl groups for $R_3$, $R_4$, $R_5$, $R_6$ and $R_7$ are $C_{6-10}$-aryl groups, e.g., phenyl, α- and β-naphthyl, preferably phenyl.

When $R_2$ is alkoxycarbonyl, suitable "alk" moieties include: methyl, ethyl, propyl, isopropyl, butyl, sec-butyl, tert-butyl, and benzyl.

When Y is N-($C_1$–$C_4$-alkyl)imino and $R_2$ is $C_1$–$C_4$-alkoxy-carbonyl or di-$C_1$–$C_4$-alkylcarbonyl, the alkyl portion is preferably to be a straight-chain alkyl of 1-4 carbon atoms (methyl, ethyl, n-propyl or n-butyl).

In-$(CR_6R_7)p$-as Q, p is an integer of 0 to 3. The compounds wherein p=0 or p=1 are preferred.

Halogen in the definition of D includes fluorine, chlorine, bromine, and iodine. Fluorine and chlorine are preferred.

From the foregoing, it can be seen that

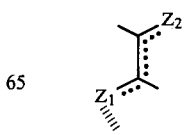

in Formula I preferably has the following structures:

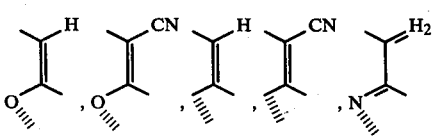

Equivalent compounds are those as described above except that free OH groups are conventionally esterified or etherified with the usual protecting groups such as tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid.

The invention furthermore relates to a process for the preparation of compounds of Formula I, comprising reacting a compound of Formula II $$R_1-COOR_{12} \qquad \text{II}$$

wherein $R_1$ is as defined above and $R_{12}$ is hydrogen, trialkylsilyl, or $C_1-C_6$-alkyl, optionally, after blocking any free hydroxy groups present, with an amine of Formula III,

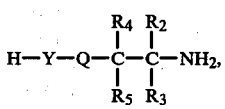

wherein $R_2$, $R_3$, $R_4$, $R_5$, Q, and Y are as defined above, using organic phosphines or phosphonium salts and perhalogenated hydrocarbons or ketones in the presence of tertiary bases and then optionally, in any desired sequence, separating isomers and/or liberating blocked hydroxy groups and/or esterifying or etherifying free hydroxy groups and/or oxidizing hydroxy groups and/or reducing oxo groups and/or hydrogenating double or triple bonds. All of the reactions included are fully conventional.

The compounds of Formula I wherein $R_1$ is a prostacyclin residue

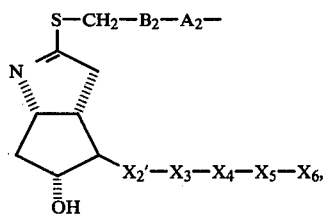

wherein $A_2$, $B_2$, $X_2'$, $X_3$, $X_4$, $X_5$, and $X_6$ are as defined above, can also be prepared by conventionally reacting the bicyclic thiolactones

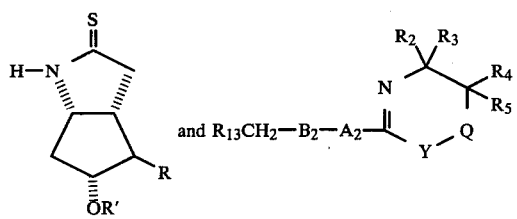

in $CH_2Cl_2$, acetonitrile, or N,N-dimethylformamide, optionally in the presence of a tertiary base, such as triethylamine, at 0°–40° C.

R and R' represent blocking groups conventional in prostacyclin chemistry; $R_{13}$ is a customary leaving group, e.g., Cl, Br, I, mesyloxy; or tosyloxy. $B_2$, $A_2$, Y, Q, $R_2$, $R_3$, $R_4$, and $R_5$ are as defined above.

As mentioned, suitable ether and acyl blocking groups for free hydroxy groups are known to persons skilled in the art. Readily cleavable ether residues are preferred, such as, for example, the tetrahydropyranyl, tetrahydrofuranyl, α-ethoxyethyl, trimethylsilyl, dimethyl-tert-butylsilyl, and tri-p-benzylsilyl residues. Suitable acyl residues are, for example, acetyl, propionyl, butyryl, benzoyl.

Suitable starting compounds II include all prostaglandins and prostacyclins which are included within $R_1$ and which have in the 1-position a $COOR_{12}$-group ($R_{12}$ being, for example, $C_1-C_6$-alkyl). Insofar as the esters of Formula II serving as starting materials are unknown, they can be readily prepared from the corresponding conventional carboxylic acids by conventional reaction with diazoalkanes in an inert solvent, preferably in diethyl ether or methylene chloride.

The trialkylsilyl esters ($R_{12}$=trialkylsilyl) are normally formed during the trialkylsilyl ether formation of the OH-groups to be blocked.

The starting material prostaglandins and prostacyclins are disclosed in many references all known to skilled workers (U.S. Pat. Nos. 4,315,013 and 4,219,479; U.S. patent application Ser. No. 086,506, filed Oct. 19, 1979 and Ser. No. 215,762, filed Dec. 10, 1980).

Preferred amines III for the cyclization to $\Delta^2$-N-heterocycles include, for the 5-membered ring series, ethanolamine, 2-aminopropanol, 2-methyl-2-aminopropanol, tris(hydroxymethyl)methylamine, o-aminophenol, cysteamine, 1,2-ethylenediamine, o-phenylenediamine, 1-amino-2-methylaminoethane, 1-amino-2-phenylaminoethane or 1-amino-2-benzylaminoethane; and for the 6-membered ring series, 3-aminopropanol 2,3,3-trimethyl-3-amino-1-propanol, 3-aminopropanethiol, 1,3-diaminopropane, and 1,3-diaminopropanes of the formula

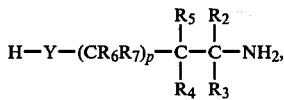

insofar as they are not specifically disclosed by name above.

All of these amines are either known or readily preparable from known compounds using fully conventional methods.

The value p determines the ring size of the $\Delta^2$-heterocycles of Formula I. Thus, there result, for example:

for p=0, $\Delta^2$-oxazolines, $\Delta^2$-thiazolines, and $\Delta^2$-imidazolines, for p=1 5,6-dihydro-4H-1,3-oxazines, 5,6-dihydro-4H-1,3-thiazines, and tetrahydropyrimidines, and for p=2 and 3, the corresponding 7- or 8-membered rings.

Suitable organic phosphines or phosphonium salts include those of the formulae $[(R_{13})_3P^{\oplus}O-R_{14}]ClO_4^{\ominus}$, $CF_3SO_3^{\ominus}$, $Cl^{\ominus}$, $Br^{\ominus}$ or $I^{\ominus}$ and $(R_{13})_2P-R_{14}$, wherein $R_{13}$ is aryl (phenyl, α- or β-naphthyl, preferably phenyl), aralkyl (of 7-10 carbon atoms as indicated above), alkyl (of 1-6 carbon atoms; see the residues for $R_2$), cycloalkyl (of 5-7 carbon atoms), O-aryl (phenyl, α- or β-naphthyl, preferably phenyl), O-alkyl (of 1-6 carbon atoms, see the residues for $R_2$), and di-($C_1$-$C_4$-alkyl)amino (preferably dimethylamino); and $R_{14}$=O—P$^{\oplus}$($C_6H_5$)$_3$; OP[N(CH$_3$)$_2$]; Cl; Br, no additional moiety; etc. Typical formulae are [($C_6H_5$)$_3$P$^{\oplus}$—O—P$^{\oplus}$($C_6H_5$)$_3$]2CF$_3$SO$_3^{\ominus}$, [[(CH$_3$)$_2$N]$_3$P$^{\oplus}$—O—P$^{\oplus}$[N(CH$_3$)$_2$]$_3$]·2CF$_3$SO$_3^{\ominus}$ and/or [[(CH$_3$)$_2$N]$_3$P$^{\oplus}$—Cl]ClO$_4^{\ominus}$.

Since the reaction velocity decreases among these reactants in the above-described sequence, $(R_{13})_3$P for $R_{13}$=aryl, preferably phenyl, is most reactive. therefore, ($C_6H_5$)$_3$P/CCl$_4$, ($C_6H_5$)$_3$P/C$_2$Cl$_6$, [($C_6H_5$)$_3$P$^{\oplus}$—O—P$^{\oplus}$($C_6H_5$)$_3$]2CF$_3$SO$_3^{\ominus}$ or [($C_6H_5$)$_3$P—Cl]Cl$^{\ominus}$; [($C_6H_5$)$_3$P$^{\oplus}$—br]Br$^{\ominus}$; [($C_6H_5$)$_3$P$^{\oplus}$—I]I$^{\ominus}$; ($C_6H_5$)$_2$P—Cl, or polymeric aromatic phosphines wherein triarylphosphines are chemically bound to a polymeric matrix, are preferred reagents.

As the electrophilic component, perhalogenated aliphatics and aralkyls, as well as carbonyl compounds can be utilized, such as CCl$_4$, CBrCl$_3$, CBr$_2$Cl$_2$, CClBr$_3$, CBr$_4$, C$_2$Cl$_6$, $C_6H_5$—CCl$_3$, CCl$_3$—CO—CCl$_3$, CCl$_3$—CH$_3$, CHBr$_3$, CCl$_3$CN, CCl$_3$—CHO, etc., but preferably CCl$_4$; usable azo esters include $R_{11}$OO—C—N=N—COOR$_{11}$, wherein $R_{11}$ is CH$_3$, C$_2$H$_5$,

CH$_2$CCl$_3$, preferably wherein $R_{11}$ is CH$_3$ or C$_2$H$_5$.

Suitable tertiary amines include, for example, trimethylamine, triethylamine, tri-n-propylamine, tributylamine, diisopropylethylamine, dicyclohexylethylamine, benzyldimethylamine, pyridine, lutidine, collidine, 2-dimethylaminopyridine, 4-dimethylaminopyridine, quinoline, 1,4-diazabicyclo[4.3.0]non-5-ene (DBN), 1,8-diaza-bicyclo[5.4.0]undec-7-ene (DBU), 1,4-diazabicyclo[2.2.2]octane (DABCO), preferably triethylamine and pyridine.

The reaction is conducted in aprotic, absolute solvents or solvent mixtures, such as CCl$_4$, chloroform, methylene chloride, benzene, toluene, diethyl ether, tetrahydrofuran, ethyl acetate, acetonitrile, dimethylformamide (DMF), or sulfolane, preferably in acetonitrile, pyridine, or DMF.

The reaction takes place at temperatures of −20° C. to 100° C., preferably at +10° C. to +30° C.

It is advantageous to use equivalent amounts of the amine component (ω-hydroxy- and ω-mercaptoamine and ω-diamine) per carboxy or ester group. The tertiary phsphine (preferably triphenylphosphine) and the electrophile (preferably CCl$_4$ or C$_2$Cl$_6$) are employed in two- to fivefold molar excesses, preferably in a three- to fourfold molar excess, based on the number of carboxy groups. At least 2-3 equivalents are required of the phosphonium salts, such as [($C_6H_5$)$_3$P$^{\oplus}$—O—P$^{\oplus}$($C_6H_5$)$_3$]2CF$_3$SO$_3^{\ominus}$.

Advantageously, 2-5 equivalents, preferably at least 4 eqivalents of the tertiary amine (preferably triethylamine) are likewise utilized. An excess of amine such as triethylamine provides improved solubility of the amine salts of the carboxylic acids.

Since the reaction of trisubstituted phosphines $(R_{13})_3$P (preferably triphenylphosphine) with halogen compounds, preferably CCl$_4$, takes place over quite a series of reaction products [see R. Appel, Angew. Chem. [Applied Chemistry] 87: 863 (1975)], and the initial reaction products, for example [($C_6H_5$)$_3$P$^{\oplus}$—CCl$_3$]Cl$^{\ominus}$ are otimal for the cyclization, it is expedient to add the triphenylphosphine, in solution (preferably in acetonitrile), gradually and drop-wise to the mixture of the other reactants, in order to attain high yields in the desired prostaglandins or prostacyclins I.

These compounds can be chromatographed on extremely deactivated adsorbents, such as, for example, aluminum oxide (A IV–V) or silica gel combined with 30-40% water, most advantageously with the use of pressure, and without the disintegration of relatively large amounts of these compounds during the chromatography.

In accordance with the process described in DOS No. 3,047,759 it is very easy to convert substituted carboxylic acids $R_1$—COOH, in the presence of amines of Formula II in combination with tert-phosphines, especially triphenylphosphine, in the presence of halogen compounds such as especially carbon tetrachloride, and a tertiary base, preferably triethylamine, DBN or DBU, or in combination with [($C_6H_5$)$_3$P$^{\oplus}$—O—P$^{\oplus}$($C_6H_5$)$_3$]2CF$_3$SO$_3^{\ominus}$, into the aforementioned 2-substituted $\Delta^2$-oxazolines, $\Delta^2$-imidazolines, and/or 5,6-dihydro-4H-1,3-oxazines, 5,6-dihydro-4H-thiazines, or tetrahydropyrimidines. During this procedure, the not-as-yet cyclized ω-hydroxy-, ω-mercapto-, or ω-aminalkylamides are formed, in all cases as intermediates which can be isolated and can be employed just as the carboxylic acids for cyclizing purposes.

Thus, it is possible, for example, to react prostaglandin F$_{2\alpha}$ very readily to the persilylated $\Delta^2$-oxazoline, after blockage of the reactive hydroxy groups by silylation (unless these hydroxy groups have been blocked previously anyway by other blocking groups, such as acyl, tetrahydropyranyl, or silyl groups) directly by reaction with ethanolamine in the presence of triphenylphosphine, carbon tetrachloride, and triethylamine in absolute acetonitrile or N,N-dimethylformamide; the trimethylsilyl blocking groups in the 9-,11- and 15-positions can easily be removed from this persilylated $\Delta^2$-oxazoline by aqueous or alcoholic alkaline solution.

However, it is likewise possible to react the starting prostaglandins and starting prostacyclins of Formula II, as well as their analogs, directly, without blockage of their hydroxy groups, to the corresponding derivatives of the 1-carboxy group, such as $\Delta^2$-oxazolines, $\Delta^2$-thiazolines, $\Delta^2$-imidazolines, as well as $\Delta^2$-oxazines, etc., under carefully controlled conditions (e.g., as discussed above) with triphenylphosphine, carbon tetrachloride, and triethylamine, especially in absolute acetonitrile, acetonitrile-pyridine, N,N-dimethylformamides or N-methylpyrrolidone, or sulfolane, without protecting these free hydroxy groups of the starting compounds and/or without converting them into their corresponding chlorine derivatives.

All of the foregoing reactions can be conducted using fully conventional procedures and considerations, e.g., as discussed in PCT/DE81/00225, which is incorporated by reference herein.

The functional modification of the free OH-groups can be effected according to methods known to those skilled in the art. In order to introduce the ether blocking groups, the reaction is conducted, for example, with dihydropyran in methylene chloride or chloroform using an acidic condensation agent, e.g. p-toluene-sulfonic acid. The dihydropyran is used in excess, preferably in four to ten times the theoretical requirement. The reaction is normally terminated at 0°–30° C. after 15–30 minutes.

The introduction of the acyl blocking groups can be effected by conventionally reacting a compound of Formula I with a carboxylic acid derivative, such as, for example, an acid chloride, an acid anhydride, and others.

The liberation of a functionally modified OH-group to obtain the compounds of Formula I can be conducted according to conventional methods. For example, the step of splitting off ether blocking groups can be carried out in an aqueous solution of an organic acid, such as, for example, acetic acid, propionic acid, etc., or in an aqueous solution of an inorganic acid, e.g. hydrochloric acid. To improve solubility, a water-miscible, inert organic solvent is suitably added. Suitable organic solvents include, for example, alcohols, such as methanol and ethanol, and ethers, such as dimethoxyethane, dioxane, and tetrahydrofuran. Tetrahydrofuran is preferably employed. The splitting-off step is conducted preferably at temperatures of 20° to 80° C.

The silyl ether blocking groups can be split off, for example, with tetrabutylammonium fluoride. Examples of suitable solvents are tetrahydrofuran, diethyl ether, dioxane, methylene chloride, etc. The splitting-off step is preferably conducted at temperatures of 0° to 80° C.

The acyl groups can be saponified, for example, with alkali or alkaline earth metal carbonates or hydroxides in an alcohol or in the aqueous solution of an alcohol. Suitable alcohols include aliphatic alcohols, such as, for example, methanol, ethanol, butanol, etc., preferably methanol. Alakli metal carbonates and hydroxides include potassium and sodium salts, but the potassium salts are preferred. Suitable alkaline earth metal carbonates and hydroxides include, for example, calcium carbonate, calcium hydroxide, and barium carbonate. The reaction is carried out at −10° to 70° C., preferably at 25° C.

The oxidation of any hydroxy groups present is effected by following conventional methods and using the customary oxidizing agents. For example, the oxidation of the 9-hydroxy group to the 9-ketone can take place with Jones reagent (J. Chem. Soc. 1953: 2555), wherein any other free hydroxy groups in the molecule, for example in the 11- and/or 15-position, are first selectively blocked in a manner known per se. An excess of oxidizing agent is employed in an inert solvent, such as acetone, using temperatures of 30° to −50° C., preferably about −20° C. The reaction is generally completed after about 5–30 minutes.

The reduction of the 9-keto group to prepare the corresponding 9β-hydroxy compounds can be effected with a reducing agent suitable for the reduction of ketones, such as, for example, sodium borohydride. The resultant mixture of epimers is separated, for example, in the usual way by column or layer chromatography.

If C=C-double bonds present in the primary product are to be reduced, the hydrogenation is conducted according to conventional methods.

For example, the hydrogenation of the 5,6-double bond is conducted in a manner known per se at low temperatures, preferably at about −20° C. in a hydrogen atmosphere in the presence of a noble metal catalyst. A suitable catalyst is, for example 10% palladium on carbon.

If the 5,6- as well as 13,14-double bond is to be hydrogenated, the process is conducted at a higher temperature, preferably at about 20° C.

The starting material bicyclic thiolactones and heterocyclic N-compounds for the alternative reaction discussed above are all known compounds or are readily preparable.

The novel prostaglandin analogs of Formula I have a very strong luteolytic activity, i.e. for triggering luteolysis, substantially smaller doses are required than in case of the corresponding natural prostaglandins.

Also, to induce abortions, especially upon oral administration, substantially smaller quantities of the novel prostaglandin analogs of this invention are necessary as compared with the natural prostaglandins.

When recording the isotonic uterine contraction on anesthetized rats and on the isolated rat uterus, it is found that the compounds of this invention are substantially more efficacious and that their effects are of a longer duration than in case of the natural prostaglandins.

The novel prostaglandin derivatives are suitable, after a single enteral or parenteral administration, for inducing menstruation or interrupting pregnancy. They are furthermore suitable for synchronizing the sexual cycle in female mammals, such as rabbits, cattle, horses, pigs, etc.

The good tissue specificity of the compounds with antifertility action, can be demonstrated in studies on other smooth-muscle organs, such as, for example, on the guinea pig ileum or on the isolated rabbit trachea, where a substantially lesser stimulation can be observed than caused by the natural prostaglandins.

The active compounds of this invention pertaining to the PGE series even show a bronchodilatory activity on the isolated rabbit trachea and greatly inhibit gastric acid secretion.

The prostacyclins of this invention have blood-pressure-lowering and bronchodilatory activity. They are furthermore suitable for inhibiting thrombocyte aggregation. Consequently, the novel prostacyclin derivatives of Formula I also constitute valuable pharmaceutically active agents. Moreover, they exhibit, with a similar spectrum of effectiveness as compared with corresponding prostaglandins, a higher specificity and, above all, a considerably longer duration of efficacy. As compared with $PGI_2$ they are distinguished by a higher stability. The high tissue specificity of the novel prostaglandins can be demonstrated in studies on smooth-muscle organs, such as, for example, on the guinea pig ileum or on the isolated rabbit trachea where a substantially lower stimulation can be observed than in the administration of natural prostaglandins of the E, A, or F type.

The novel prostacyclin analogs possess the properties typical for prostacyclins, such as, for example, lowering of peripheral arterial and coronary vascular resistance, inhibition of thrombocyte aggregation, and dissolution of platelet thrombi, myocardial cytoprotection, and thus lowering of systemic blood pressure without simultaneously lowering stroke volume and coronary blood flow; they are suitable for treatment of strokes, prophylaxis and therapy of coronary heart disease, coronary thrombosis, cardiac infarction, peripheral arterial diseases, arteriosclerosis and thrombosis, shock therapy, inhibition of bronchonstriction, inhibition of gastric acid secretion, cytoprotection of gastric and intestinal mucosa; they exhibit antiallergic properties, lowering of pulmonary vascular resistance and pulmonary blood pressure, promotion of kidney blood blood flow, utilization in place of heparin or as adjuvants in dialysis of hemofiltration, preservation of blood plasma stores, especially blood platelet preserves, inhibition of labor, treatment of gestational toxicoses, enhancement of cerebral blood flow, etc. Furthermore, the novel prostacyclin analogs exhibit antiproliferative properties and show cytoprotective effects on liver and pancreas. They are furthermore suitable for prophylaxis and therapy of ischemic attacks on the central nervous system. Thus, the novel compounds of this invention are substantially more selective with regard to potency, as compared with known PG analogs in causing prostaglandin-like biological responses, and have a substantially longer duration of biological activity. Accordingly, each of these analogs is surprisingly and unexpectedly more useful than one of the corresponding conventional prostaglandins for at least one of the pharmacological purposes indicated above because it has a different and narrower spectrum of biological potency than the known prostaglandins, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Typical dosages of the compounds of this invention are 1-1500 μg/kg/day, e.g., when administered orally to mammals, including human patients. The unit dosage for the pharmaceutically acceptable vehicles is typically 0.01-100 mg. They can be administered by analogy to known agents such as $PGE_2$ or $PGI_2$.

When administered orally to nonanesthetized, hypertonic rats in doses from 100 to 500 μg/kg body weight, the compounds of this invention show a stronger hypotensive activity of a longer duration than $PGE_2$ and $PGA_2$ without triggering diarrhea, as does $PGE_2$, or cardiac arrhythmias, as does $PGA_2$.

Sterile, injectable, aqueous or oily solutions can be used for parenteral administration. Suitable for oral administration are, for example, tablets, dragees, or capsules.

Consequently, the invention also concerns medicinal agents based on the compounds of Formula I and customary auxiliary agents and excipients. For example, the active agents of this invention can serve, in conjunction with the auxiliary agents known and conventional in galenic pharmacy, for the preparation of hypotensive drugs.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5Z,13E)-(8R,9S,11R,12R,15S)-9,11-15-Triacetoxy-2-(2-oxazolin-2-yl)-1-nor-5,13-prostadiene 207 mg (0.43 millimole) of 9,11,15-triacetylprostaglandin-$F_{2\alpha}$ is dissolved in 2 ml of absolute acetonitrile and combined with 0.43 ml of a molar solution of ethanolamine in acetonitrile, 394 mg (1.5 mmol) of triphenylphosphine, and 5.3 ml of a molar solution of triethylamine in acetonitrile. The slightly yellowish, clear solution is cooled to 2° C. internal temperature. Within 5 minutes, 0.86 ml of a molar solution of carbon tetrachloride in acetonitrile is added dropwise to the mixture and the latter is then stirred for 4 hours at 2° C. After 48 hours of standing at room temperature, the reaction mixture is concentrated without heating and extracted four times with respectively 15 ml of distilled hexane. Concentration and crystallization of the triphenylphosphine oxide from hexane yield 196 mg (90.2% of theory) of the title compound.

EXAMPLE 2

(5Z,13E)-(8R,9S,11R,12R,15S)-2-(2-Oxazolin-2-yl)-1-nor-5,13-prostadiene-9,11,15-triol 516 mg (1 mmol) of the compound produced according to Example 1 is dissolved in 15 ml of methanol, the solution is cooled to 0° C. and combined with 15 ml of 2N NaOH. After 30 minutes of agitation in an ice bath, the mixture is stirred for 2 hours at room temperature. After gentle concentration of the reaction solution on a forced circulation evaporator at 25° C. to about 10 ml, it is diluted with 10 ml of water and extracted four times with respectively 20 ml of ethyl acetate. After drying over $Na_2SO_4$ and concentration, the compound, taken up in methylene chloride, is separated by preparative procedure on silica gel with chloroform/methanol (9:1) as the eluent, and then eluted first with ethanol and then three times with a small amount of carbon tetrachloride. Yield: 178 mg (46.9% of theory).

EXAMPLE 3

(5Z,13E)-(8R,9S,11R,12R,15S)-2-(2-Oxazolin-2-yl)-1-nor-5,13-prostadiene-9,11,15-triol 177 mg (0.5 mmol) of prostaglandin $F_{2\alpha}$ is suspended in 5 ml of distilled hexamethyldisilazane (HMDS), thus forming a clear colorless solution, under evolution of $NH_3$ and heating, after 30 minutes. After 1.5 hours of heating at a bath temperature of 140° C., excess HMDS is evaporated under vacuum and the residue dried for 30 minutes at a bath temperature of 40° C. and under 0.2 millibar on an oil pump.

The residue is dissolved in 5 ml of absolute acetonitrile, 786 mg (3 mmol) of triphenylphosphine and 1.05 ml (7.5 mmol) of triethylamine are added, and, under ice cooling, 0.5 ml of a molar solution of ethanolamine in acetonitrile is added dropwise. Thereafter 1.5 ml of a molar solution of carbon tetrachloride in acetonitrile is added to the mixture and the latter is allowed to stand overnight at room temperature. After concentration under vacuum, the mixture is washed five times with respectively 75 ml of hexane. The thus-formed crystals are separated from the oily residue, and the latter is taken up in 15 ml of methanol and combined under cooling with 5 ml of 2N NaOH, and then stirred for 30 minutes at 20° C. After concentration under vacuum to about 5 ml, the mixture is combined with 10 ml of water and extracted four times with respectively 10 ml of ethyl acetate. After drying the ethyl acetate phases with $Na_2SO_4$ and concentration, 208 mg of a light-brown, oily residue remains. After preparative thin-layer chromatography on $SiO_2$ with chloroform/methanol (9:1) as the eluent, the mixture is eluted with 300 ml of ethanol, concentrated, and dried on an oil pump for 1 hour at 20° C. and under 1.5 millibar. Yield: 103 mg (54.2% of theory).

EXAMPLE 4

(5Z,13E)-(8R,9S,11R,12R,15S)-2-(2-Oxazolin-2-yl)-1-nor-5,13-prostadiene-9,11,15-triol 177 mg (0.5 mmol) of prostaglandin $F_{2\alpha}$ is dissolved in 15 ml of absolute acetonitrile and combined under argon with 0.7 ml of triethylamine, 0.5 ml of a molar solution of ethanolamine in acetonitrile and 0.5 ml of carbon tetrachloride. Within 8 hours at about 20° C., 655 mg (2.5 mmol) of triphenylphosphine in 15 ml of absolute acetonitrile is added dropwise under agitation. The mixture is then stirred for another 20 hours at 20° C. After concentration under vacuum, the residue is taken up in 20 ml of ethyl acetate and 15 ml of water, and the aqueous phase is additionally extracted three times with respectively 10 ml of ethyl acetate. The combined ethyl acetate phases are dried over $Na_2SO_4$ and concentrated. Chromatography of the ethyl acetate solution (10 ml) with water-saturated ethyl acetate on $Al_2O_3$ (alkaline, activity IV) yields 127 mg (66.9% of theory) of the title compound as an oil.

EXAMPLE 5

(5Z,13E)-(8R,9S,11R,12R,15S)-2-(4,4-Dimethyl-2-oxazolin-2-yl)-1-nor-5,13-prostadiene-9,11,15-triol Analogously to Example 3, 177 mg (0.5 mmol) of prostaglandin $F_{2\alpha}$ is reacted with 0.5 ml of a molar solution of 2-amino-2-methyl-1-propanol in acetonitrile. Yield: 98 mg (48.3% of theory).

EXAMPLE 6

(5Z,13E)-(8R,9S,11R,12R,15S)-2-(2-Thiazolin-2-yl)-1-nor-5,13-prostadiene-9,11,15-triol Analogously to Example 3 from 177 mg (0.5 mmol) of prostaglandin $F_{2\alpha}$ and 57 mg (0.5 mmol) of 2-aminoethanethiol hydrochloride under argon. Yield: 113 mg (57% of theory).

EXAMPLE 7

1-Decarboxy-2-(oxazolin-2-yl)-(5R,6R)-5-bromoprostaglandin-$I_1$

Analogously to Example 4 from 216 mg (0.5 mmol) of (5R,6R)-5-bromoprostaglandin-$I_1$ and ethanolamine. Yield: 125 mg (54.4% of theory).

EXAMPLE 8

1-Decarboxy-2-(oxazolin-2-yl)prostaglandin-$I_2$ 25 mg (0.27 mmol) of the compound prepared according to Example 7 is combined with 5 ml of absolute toluene and, under argon, 0.25 ml of DBU is added. After 8 hours of agitation at 60°–65° C., concentration, chromatography on $SiO_2$ with ethyl acetate/methanol (9:1), 43 mg (42.3% of theory) of a light-yellow, viscous oil is obtained.

EXAMPLE 9

2-{4-{(E)-(1S,5S,6R,7R)-7-Hydroxy-6-[(E)-(3S,4RS)-3-hydroxy-4-methyloct-1-en-6-ynyl]bicyclo[3.3.0]octan-3-ylidene)}-butyl}-2-oxazoline Analogously to Example 4 from 50 mg (0.14 mmol) of 5-{(E)-(1S,5S,6R,7R)-7-hydroxy-6-[(E)-(4RS)-3α-hydroxy-4-methyloct-1-en-6-ynyl]bicyclo[3.3.0]octan-3-ylidene}pentanoic acid and ethanolamine under argon. Yield: 16 mg (29.6% of theory).

EXAMPLE 10

2-{(E)-(1S,5R,6R)-7-Hydroxy-6-[(E)-(3S,4RS)-3-hydroxy-4-methyl-1-octenyl]-2-oxabicyclo[3.3.0]octan-3-ylidene}-5-(2-oxazolin-2-yl)pentanenitrile Analogously to Example 4 from 78 mg (0.2 mmol) of 5-cyano-5-{(1S,5R,6R)-7-hydroxy-6-[(E)-(3S,4RS)-3-hydroxy-4-methyl-1-octenyl]-2-oxabicyclo[3.3.0]octan-3-ylidene}-pentanoic acid and ethanolamine. Yield: 60 mg (72% of theory).

EXAMPLE 11

2-Aza-3-[1-thia-4-(2-oxazolin-2-yl)butyl]-6-(3α-acetoxy-1-octenyl)-7α-acetoxybicyclo[3.3.0]octene-2

195 mg (0.43 mmol) of 2-aza-3-(1-thia-4-carboxybutyl)-6-(3α-acetoxy-1-octenyl)-7α-acetoxybicyclo[3.3.0]octene-2 is dissolved in 2 ml of absolute acetonitrile and combined with 0.43 ml of a molar solution of ethanolamine in acetonitrile, 394 mg (1.5 mmol) of triphenylphosphine, and 5.3 ml of a molar solution of triethylamine in acetonitrile. The slightly yellowish, clear solution is cooled to 2° C. internal temperature. Within 5 minutes, 0.86 ml of a molar solution of carbon tetrachloride in acetonitrile is added dropwise thereto, and the mixture is stirred thereafter for 4 hours at 2° C. After allowing the mixture to stand for 48 hours at room temperature, it is concentrated without heating and extracted four times with respectively 15 ml of distilled hexane. After concentration and crystallization of the triphenylphosphine oxide from hexane, 172.8 mg (80.6% of theory) of the title compound is obtained.

EXAMPLE 12

2-Aza-3-[1-thia-4-(2-oxazolin-2-yl)butyl]-6-(3α-hydroxy-1-octenyl)-7α-hydroxybicyclo[3.3.0]octene-2

498.6 mg (1 mmol) of the compound prepared according to Example 1 is dissolved in 15 ml of methanol; the solution is cooled to 0° C. and then combined with 15 ml of 2N NaOH. After 30 minutes of agitation in an ice bath, the mixture is stirred for 2 hours at room temperature. After gentle concentration of the reaction solution on a forced circulation evaporator at 25° C. to about 10 ml, the mixture is diluted with 10 ml of water and extracted four times with respectively 20 ml of ethyl acetate. After drying over $Na_2SO_4$ and concentration, the compound is taken up in methylene chloride and preparatively separated on silica gel with chloroform/methanol (9:1) as the eluent, by first eluting with ethanol and then three times with a small amount of carbon tetrachloride. Yield: 213.5 mg (54.1% of theory).

EXAMPLE 13

2-Aza-3-[1-thia-4-(2-oxazolin-2-yl)butyl]-6-(3α-trimethylsilyloxy-1-octenyl)-7α-trimethylsilyloxybicyclo[3.3.0]octene-2

184.7 mg (0.5 mmol) of 2-aza-3-(1-thia-4-carboxybutyl)-6-(3α-hydroxy-1-octenyl)-7α-hydroxybicyclo[3.3.0]octene-2 is suspended in 5 ml of distilled hexamethyldisilazane (HMDS), thus forming a clear, colorless solution under evolution of $NH_3$ and heating after 30 minutes. After 1.5 hours of heating at a bath temperature of 140° C., excess HMDS is withdrawn under vacuum and the residue is dried on an oil pump for 30 minutes at a bath temperature of 40° C. and under 0.2 millibar.

The residue is dissolved in 5 ml of absolute acetonitrile; 786 mg (3 mmol) of triphenylphosphine and 1.05 ml (7.5 mmol) of triethylamine are added, and the mixture is combined dropwise under ice cooling with 0.5 ml of a molar solution of ethanolamine in acetonitrile. Then 1.5 ml of a molar solution of carbon tetrachloride in acetonitrile is added thereto and the mixture is allowed to stand overnight at room temperature. After concentration under vacuum, the mixture is washed five times with respectively 75 ml of hexane. The evolving crystals are separated and the oily residue is dried for 1 hour at 20° C. and under 1.5 millibar. Yield: 234.7 mg (87.1% of theory).

EXAMPLE 14

2-Aza-3-[1-thia-4-(2-oxazolin-2-yl)butyl]-6-(3α-hydroxy-1-octenyl)-7α-hydroxybicyclo[3.3.0]octene-2

215.6 mg (0.4 mmol) of the compound prepared according to Example 3 is taken up in 15 ml of methanol and combined under cooling with 5 ml of 2N NaOH and thereafter stirred for 30 minutes at 20° C. After concentration under vacuum to about 5 ml, the mixture is combined with 10 ml of water and extracted four times with respectively 10 ml of ethyl acetate. After drying the ethyl acetate phases with $Na_2SO_4$ and concentration, 208 mg of a light-brown, oily residue remains. After preparative thin-layer chromatography on $SiO_2$ with chloroform/methanol (9:1) as the eluent, the mixture is eluted with 300 ml of ethanol, concentrated, and dried on an oil pump for 1 hour at 20° C. and under 1.5 millibar. Yield: 90.3 mg (57.2% of theory).

EXAMPLE 15

2-Aza-3-[1-thia-4-(2-oxazolin-2-yl)butyl]-6-(3α-hydroxy-4(R,S)-methyl-1-octenyl)-7α-hydroxybicyclo[3.3.0]octene-2

Analogously to Example 1 from 187 mg (0.4 mmol) of 2-aza-3-(1-thia-4-carboxybutyl)-6-(3α-acetoxy-4(R,S)-methyl-1-octenyl)-7α-acetoxybicyclo[3.3.0]octene-2 and subsequent saponification of the isolated 2-aza-3-[1-thia-4-(2-oxazolin-2-yl)butyl]-6-(3α-acetoxy-4(R,S)-methyl-1-octenyl)-7α-acetoxybicyclo[3.3.0]octene-2 with $NaOH/CH_3OH$ analogously to Example 2. Yield: 80.9 mg (49.5% of theory).

EXAMPLE 16

2-Aza-3-[1-thia-4-(2-oxazolin-2-yl)butyl]-6-(3α-hydroxy-4,4-dimethyl-1-octenyl)-7α-hydroxybicyclo[3.3.0]octene-2

Analogously to Example 1 from 192.65 mg (0.4 mmol) of 2-aza-3-(1-thia-4-carboxybutyl)-6-(3α-acetoxy-4,4-dimethyl-1-octenyl)-7α-acetoxybicyclo[3.3.0]octene-2 and subsequent saponification of the bisacetoxy compound analogously to Example 2. Yield: 70.8 mg (41.9% of theory).

EXAMPLE 17

2-Aza-3-[1-thia-4-(2-oxazolin-2-yl)butyl]-6-(3α-hydroxy-4-methyl-6,7-tetradehydro-1-nonenyl)-7α-hydroxybicyclo-[3.3.0]octene-2

Analogously to Example 1 from 143.3 mg (0.3 mmol) of 2-aza-3-(1-thia-4-carboxybutyl)-6-(3α-acetoxy-4-methyl-6,7-tetradehydro-1-nonenyl)-7α-acetoxybicyclo[3.3.0]octene-2 and subsequent saponification of the bisacetoxy compound analogously to Example 2. Yield: 60 mg (47.8% of theory).

EXAMPLE 18

2-Aza-3-{1-thia-4-[2-(5,6-dihydro-4H-1,3-oxazin-2-yl)]-butyl}-6-(3α-hydroxy-4-phenoxy-1-butenyl)-7α-hydroxybicyclo[3.3.0]octene-2

Analogously to Example 1 from 244.8 mg (0.5 mmol) of 2-aza-3-(1-thia-4-carboxybutyl)-6-(3α-acetoxy-4-phenoxy-1-butenyl)-7α-acetoxybicyclo[3.3.0]octene-2 and 3-aminopropanol and subsequent saponification of the bisacetoxy compound analogously to Example 2. Yield: 120.7 mg (54.3% of theory).

EXAMPLE 19

2-Aza-3-[1-thia-3,3-difluoro-4-(2-thiazolin-2-yl)butyl]-6-(3α-hydroxy-5-phenyl-1-pentenyl)-7α-hydroxybicyclo[3.3.0]octene-2

Analogously to Example 1 from 261.8 mg (0.5 mmol) of 2-aza-3-(1-thia-3,3-difluoro-4-carboxybutyl)-6-(3α-acetoxy-4-phenyl-1-pentenyl)-7α-acetoxybicyclo[3.3.0]-octene-2 and cysteamine and subsequent saponification of the bisacetoxy compound analogously to Example 2. Yield: 126.2 mg (51.9% of theory).

EXAMPLE 20

2-Aza-3-[1-thia-4-(2-imidazolin-2-yl)butyl]-6-[3α-hydroxy-4-(3-chlorophenoxy)-1-butynyl]-7α-hydroxybicyclo[3.3.0]-octene-2

Analogously to Example 1 from 261 mg (0.5 mmol) of 2-aza-3-(1-thia-4-carboxybutyl)-6-[3α-acetoxy-4-(3-chlorophenoxy)-1-butynyl]-7α-acetoxybicyclo[3.3.-0]octene-2 and 1,2-diaminoethane and subsequent saponification of the bisacetoxy compound analogously to Example 2. Yield: 112.7 mg (48.8% of theory).

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

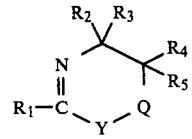

wherein $R_1$ is a prostacyclin residue of the formula

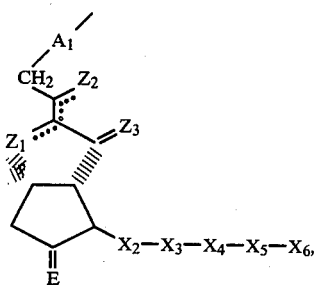

wherein
E is oxygen; hydrogen and α-hydroxy; hydrogen and α—CH₃; or hydrogen and α—CH₂OH;
X₂ is —CH₂—CH₂—, —C≡C—, or trans-alkenylene of the formula

wherein R₈ and R₉ each independently is hydrogen or $C_1$-$C_6$-alkyl;
X₃ is

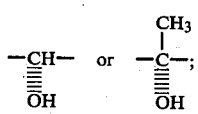

X₄ is —(CH₂)$_n$—, wherein n is an integer of 1–3, or

wherein R₁₀ and R₁₁ each independently is hydrogen, fluorine, methyl or methoxy, or R₁₀ and R₁₁ jointly represent —CH₂—CH₂— or —CH₂—CH₂—CH₂—;
X₅ is —CH₂—, oxygen, sulfur, or a direct bond; and
X₆ is phenyl, 3- or 4-chlorophenyl, 3-trifluoromethylphenyl, α- or β-naphthyl, 2- or 3-furyl, 2- or 3-thienyl, 2-, 3-, or 4-pyridyl or, when X₅ is a direct bond, X₆ is

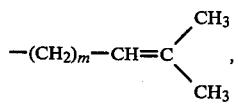

—(CH₂)$_m$—C≡C—CH₃ or —(CH₂)$_m$—C≡C—CH₂—CH₃, wherein m is an integer of 1–2, —(CH₂)₄—OCH₃, —CH(CH₃)—CH₂—CH₂—CH₃—CH₂—CH₂—CH₂—CH₃ or —(CH₂)₃—CH=CH₂;
A₁ is —(CH₂)$_n$—, —(CH₂)$_m$—O—, —CF₂—(CH₂)$_m$—, wherein n is an integer of 1–3 and m is an integer of 1–2,
—CH=CH—CH₂— or —CH₂—CH=CH—, and
Z₃ is H₂ or oxygen;

(i) Z₁ is oxygen or CH₂ when Z₂ is hydrogen, or cyano; or
(ii) Z₁ is nitrogen when Z₂ is H₂; or
(III) R₁ is a prostacyclin residue of the formula

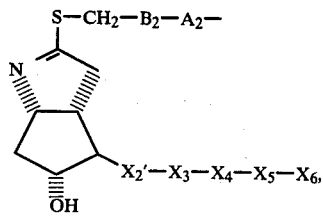

wherein
A₂ is —CH₂—, —CF₂—,

or when B₂ is a direct bond, can also be trans-alkenylene of the formula

B₂ is —CH₂— or a direct bond,
X₂' is —CH₂—CH₂—, —C≡C—, or trans-alkenylene of formula

wherein R₈' and R₉' in each case are independently hydrogen or fluorine, and
X₃-X₆ are as defined above, and
in all of the foregoing, Y is oxygen, sulfur, imino, or N-($C_1$-$C_4$-alkyl)imino;
Q is (CR₆R₇)$_p$ wherein p is an integer of 0 to 3,
R₂ is hydrogen; alkyl of 1–6 carbon atoms; alkyl of 1–6 carbon atoms substituted by hydroxy, amino, nitro, fluorine, chlorine, bromine, $C_1$-$C_4$-alkoxycarbonyl, di-$C_1$-$C_4$-alkylaminocarbonyl, $C_1$-$C_4$-alkylaminocarbonyl, tri-$C_1$-$C_4$-alkylsilyloxy, tetrahydropyranyloxy, or benzoyloxy; $C_1$-$C_4$-alkoxycarbonyl; benzyloxycarbonyl; cyano; or di-$C_1$-$C_4$-alkylaminocarbonyl;
R₃, R₄, R₅, R₆ and R₇ each independently is hydrogen; alkyl of 1–6 carbon atoms; alkyl of 1–6 carbon atoms substituted as recited for R₂; or $C_{6-10}$-aryl; and
R₃ and R₄ together also can form trimethylene, tetramethylene, or 1,3-butadienylene when R₂ and R₅ jointly represent an additional bond;
or a corresponding compound wherein in at least one OH group, the H atom is replaced by tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid.

2. A compound of claim 1 wherein

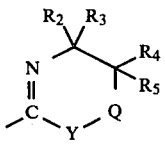

is 2-oxazolin-2-yl, 4,4-dimethyl-2-oxazolin-2-yl, 2-thiazolin-2-yl, 2-(5,6-dihydro-4H-1,3-oxazin-2-yl), or 2-imidazolin-2-yl.

3. A compound of claim 1 wherein $R_1$ has the basic structure of $PGF_{2\alpha}$, PGI, $PGI_2$, carbo-$PGI_2$, or

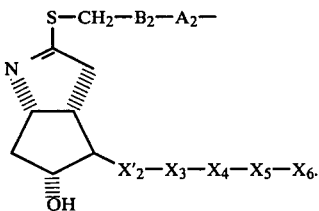

4. 1-Decarboxy-2-(oxazolin-2-yl)-(5R,6R)-5-bromoprostaglandin-$I_1$.

5. 1-Decarboxy-2-(oxazolin-2-yl)-prostaglandin-$I_2$, a compound of claim 1.

6. 2-{4-{(E)-(1S,5S,6R,7R)-7-Hydroxy-6-[(E)-(3S,4RS)-3-hydroxy-4-methyloct-1-en-6-ynyl]bicyclo[3.3.0]-octan-3-ylidene)}butyl}-2-oxazoline, a compound of claim 1.

7. 2-{(E)-(1S,5R,6R)-7-Hydroxy-6-[(E)-(3S,4RS)-3-hydroxy-4-methyl-1-octenyl]-2-oxabicyclo[3.3.0]octan-3-ylidene}-5-(2-oxazolin-2-yl)-pentanenitrile, a compound of claim 1.

8. 2-Aza-3-[1-thia-4-(2-oxazolin-2-yl)butyl]-6-(3α-hydroxy-1-octenyl)-7α-hydroxybicyclo[3.3.0]octene-2, a compound of claim 1.

9. 2-Aza-3-[1-thia-4-(2-oxazolin-2-yl)butyl]-6-(3α-acetoxy-1-octenyl)-7α-acetoxybicyclo[3.3.0]octene-2, a compound of claim 1.

10. 2-Aza-3-[1-thia-4-(2-oxazolin-2-yl)butyl]-6-(3α-trimethylsilyloxy-1-octenyl)-7α-trimethylsilyloxybicyclo[3.3.0]octene-2, a compound of claim 1.

11. 2-Aza-3-[1-thia-4-(2-oxazolin-2-yl)butyl]-6-(3α-hydroxy-4(RS)-methyl-1-octenyl)-7α-hydroxybicyclo[3.3.0]octene-2, a compound of claim 1.

12. 2-Aza-3-3-[1-thia-4-(2-oxazolin-2-yl)butyl]-6-(3α-hydroxy-4,4-dimethyl-1-octenyl)-7α-hydroxybicyclo[3.3.0]octene-2, a compound of claim 1.

13. 2-Aza-3-[1-thia-4-(2-oxazolin-2-yl)butyl]-6-(3α-hydroxy-4-methyl-6,7-tetradehydro-1-nonenyl)-7α-hydroxybicyclo[3.3.0]octene-2, a compound of claim 1.

14. 2-Aza-3-{1-thia-4-[2-(5,6-dihydro-4H-1,3-oxazin-2-yl)]butyl}-6-(3α-hydroxy-4-phenoxy-1-butenyl)-7α-hydroxybicyclo[3.3.0]octene-2, a compound of claim 1.

15. 2-Aza-3-[1-thia-3,3-difluoro-4-(2-thiazolin-2-yl)butyl]-6-(3α-hydroxy-5-phenyl-1-pentenyl)-7α-hydroxybicyclo[3.3.0]octene-2, a compound of claim 1.

16. 2-Aza-3-[1-thia-4-(2-imidazolin-2-yl)butyl]-6-(3α-hydroxy-4-(3-chlorophenoxy)-1-butynyl)-7α-hydroxybicyclo[3.3.0]octene-2, a compound of claim 1.

17. 2-Aza-3-[1-thia-4-(2-oxazolin-2-yl)butyl]-6-(3α-hydroxy-1-octenyl)-7α-hydroxybicyclo[3.3.0]octene-2, a compound of claim 1.

18. A pharmaceutical composition comprising a luteolytically effective amount of a compound of claim 1 and a pharmaceutically acceptable carrier.

19. A compound of claim 1 wherein $X_4$ is —$(CH_2)_n$—, —$CR_{10}R_{11}$— wherein $R_{10}$ and $R_{11}$ each independently is H, F, or methyl or $R_{10}$ and $R_{11}$ jointly represent —$CH_2$—$CH_2$— or —$CH_2$—$CH_2$—$CH_2$.

20. A compound of claim 1 wherein p is 0 or 1.

21. A compound of claim 1 wherein p is 0.

22. A compound of claim 19 wherein p is 0 or 1.

23. A compound of claim 19 wherein p is 0.

24. A pharmaceutical composition comprising a hypotensively effective amount of a compound of claim 1 and a pharmaceutically acceptable carrier.

25. A method of achieving a luteolytic effect in a patient in need of such treatment comprising administering a luteolytically effective amount of a compound of claim 1 to the patient.

* * * * *

UNITED STATES PATENT AND TRADEMARK OFFICE
CERTIFICATE OF CORRECTION

PATENT NO. : 4,468,395

DATED : August 28, 1984

INVENTOR(S) : Vorbrugen et al.

It is certified that error appears in the above-identified patent and that said Letters Patent is hereby corrected as shown below:

Claim 3, line 2, Delete "PGF$_{2\alpha}$"

Signed and Sealed this

Thirteenth Day of January, 1987

Attest:

DONALD J. QUIGG

*Attesting Officer*  *Commissioner of Patents and Trademarks*